US010093911B2

(12) United States Patent
Besenmatter et al.

(10) Patent No.: US 10,093,911 B2
(45) Date of Patent: *Oct. 9, 2018

(54) SUBTILISIN VARIANTS AND POLYNUCLEOTIDES ENCODING SAME

(71) Applicant: Novozymes A/S, Bagsvaerd (DK)

(72) Inventors: Werner Besenmatter, Vienna (AT);
Marco Malten, Copenhagen (DK);
Benie Astrid, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 272 days.

This patent is subject to a terminal disclaimer.

(21) Appl. No.: 14/376,993

(22) PCT Filed: Feb. 14, 2013

(86) PCT No.: PCT/EP2013/052964
§ 371 (c)(1),
(2) Date: Aug. 6, 2014

(87) PCT Pub. No.: WO2013/120948
PCT Pub. Date: Aug. 22, 2013

(65) Prior Publication Data
US 2015/0004671 A1 Jan. 1, 2015

Related U.S. Application Data

(60) Provisional application No. 61/601,628, filed on Feb. 22, 2012.

(30) Foreign Application Priority Data

Feb. 17, 2012 (EP) .................... 12155956

(51) Int. Cl.
*C12N 9/54* (2006.01)
(52) U.S. Cl.
CPC ........ *C12N 9/54* (2013.01); *C12Y 304/21062* (2013.01)
(58) Field of Classification Search
None
See application file for complete search history.

(56) References Cited

U.S. PATENT DOCUMENTS

| 5,352,604 | A | 10/1994 | Wilson et al. | |
| 6,436,690 | B1 * | 8/2002 | Brode, III | A61K 8/66 435/222 |
| 6,440,717 | B1 * | 8/2002 | Brode, III | A61K 8/66 435/222 |
| 6,599,730 | B1 | 7/2003 | Brode, III | |
| 2006/0259995 | A1 | 11/2006 | Cayouette et al. | |
| 2006/6259995 | | 11/2006 | Cayouette et al. | |
| 2010/0192985 | A1 * | 8/2010 | Aehle | C11D 3/386 134/26 |
| 2011/0251073 | A1 * | 10/2011 | Cascao-Pereira | A23K 1/1653 506/2 |

FOREIGN PATENT DOCUMENTS

| WO | 94/02618 A1 | 2/1994 |
| WO | 2000/037621 A1 | 6/2000 |
| WO | 2000/037627 A1 | 6/2000 |
| WO | 01/44452 A1 | 6/2001 |
| WO | 2001/081556 A2 | 11/2001 |
| WO | 2004/041979 A2 | 5/2004 |
| WO | 2004/099401 A1 | 11/2004 |
| WO | 2009037258 A1 | 3/2009 |

OTHER PUBLICATIONS

Yamagata et al, Bio Sci Biotechnol Biochem, vol. 64, No. 9, pp. 1947-1957 (2000).
Faraco et al., Microbiology, vol. 151, No. 2, pp. 457-466 (2005).
Ford et al., Protein Expression and Purification, vol. 2, pp. 95-107 (1991).
Gallagher et al., Proteins: Structure, Function, and Genetics, vol. 16, No. 2, pp. 205-213 (1993).
Martin, J. Ind. Microbiol. Biotechnol., vol. 30, pp. 568-576 (2003).
Michelle et al., BMC Evolutionary Biology, vol. 9, No. 168, pp. 1-13 (2009).
Pantoliano et al., Biochemistry, vol. 28, No. 18, pp. 7205-7213 (1989).

* cited by examiner

*Primary Examiner* — Anand U Desai
(74) *Attorney, Agent, or Firm* — David Fazzolare

(57) ABSTRACT

The present invention relates to subtilisin variants and methods for obtaining subtilisin variants. The present invention also relates to polynucleotides encoding the variants; nucleic acid constructs, vectors, and host cells comprising the polynucleotides; and methods of using the variants.

19 Claims, No Drawings

Specification includes a Sequence Listing.

SUBTILISIN VARIANTS AND POLYNUCLEOTIDES ENCODING SAME

CROSS-REFERENCE TO RELATED APPLICATIONS

This application is a 35 U.S.C. 371 national application of PCT/EP2013/052964 filed Feb. 14, 2013 which claims priority or the benefit under 35 U.S.C. 119 of European application no. 12155956.1 filed Feb. 17, 2012 and U.S. provisional application No. 61/601,628 filed Feb. 22, 2012 the contents of which are fully incorporated herein by reference.

REFERENCE TO A JOINT RESEARCH AGREEMENT

The inventions claimed in the present application were made under a joint research agreement between Henkel AG & Co. KGaA and Novozymes A/S.

REFERENCE TO A SEQUENCE LISTING

This application contains a Sequence Listing in computer readable form, which is incorporated herein by reference.

BACKGROUND OF THE INVENTION

Field of the Invention

The present invention relates to novel subtilisin variants exhibiting alterations relative to the parent subtilisin in one or more properties including: wash performance, thermal stability, storage stability or catalytic activity. The variants of the invention are suitable for use in e.g. cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention.

Description of the Related Art

In the detergent industry, enzymes have for more than 30 years been implemented in washing formulations. Enzymes used in such formulations comprise proteases, lipases, amylases, cellulases, mannosidases as well as other enzymes or mixtures thereof. Commercially the most important enzymes are proteases.

An increasing number of commercially used proteases are protein engineered variants of naturally occurring wild type proteases, e.g. Everlase®, Relase®, Coronase®, Ovozyme®, Polarzyme®, Liquanase®, Liquanase Ultra® and Kannase® (Novozymes a/s), Maxacal®, Properase®, Purafast®, Purafect OXP®, FN3®, FN4® and Excellase® (DuPont/Genencor International, Inc.) and BLAP (FIG. 29, U.S. Pat. No. 5,352,604) (Henkel AG & Co. KGaA).

Further, a number of variants are described in the art, such as in WO 04/041979 (NOVOZYMES A/S) which describes subtilisin variants exhibiting alterations relative to the parent subtilisin in e.g. wash performance, thermal stability, storage stability or catalytic activity. The variants are suitable for use in e.g. cleaning or detergent compositions.

A number of useful subtilisin variants have been described many of which have provided improved activity, stability, and solubility in different detergents. WO 94/02618 describes subtilisin variants with improved storage stability. The substitutions L211X and N212Z wherein X is any amino acid except L and Z is any amino acid except N are mentioned together with several other mutations. However, no wash performance is shown for these variants and nothing is mentioned in relation to specific stains such as egg stains. It is well known in the art that egg stains are particularly difficult to completely remove and although several protease variants with improved performance on egg stains have been described e.g. in WO 01/44452 there is still a need for proteases which have high wash performance on various stains including egg stains.

It is therefore an object of the present invention to provide variants of a protease with improved properties compared to its parent protease.

SUMMARY OF THE INVENTION

The present invention relates to subtilisin variants having protease activity, comprising the substitutions corresponding to Y217X and N218Z of SEQ ID NO: 2, wherein X and Z are selected from the group consisting of K, H, R, D, E, S and T. Thus one aspect of the invention relates to subtilisin variants having protease activity comprising the substitutions corresponding to Y217X and N218Z of SEQ ID NO: 2, wherein X and Z are selected from the group consisting of K, H, R, D, E, S and T, wherein when X is either D, E, S or T then Z is also selected from D, E, S or T and wherein when X is either K, H or R then Z is also selected from K, H or R. The present invention also relates to subtilisin variants having protease activity comprising the substitutions corresponding to Y217X and N218Z of SEQ ID NO: 2, wherein X and Z are selected from the group consisting of K, H, R, D, E, S and T and wherein when X is either D, E, S or T then Z is also selected from D, E, S or T, wherein when X is either K, H or R then Z is also selected from K, H or R and wherein the variants has an amino acid sequence which is at least 60% identical to SEQ ID NO: 2 and/or 4.

The present invention also relates to isolated polynucleotides encoding the variants; nucleic acid constructs, vectors, and host cells comprising the polynucleotides; and methods of producing the variants.

The present invention also relates to a method for obtaining a variant having protease activity of a subtilisin parent protease, comprising introducing into a parent subtilisin the substitutions corresponding to Y217X and N218Z of SEQ ID NO: 2, wherein X and Z are selected from the group consisting of D, E, R, K, H, S and T, wherein when X is either D, E, S or T then Z is also selected from D, E, S or T and wherein when X is either K, H or R then Z is also selected from K, H or R; recovering the variant and testing if said variant has protease activity. Preferably the variants have at least 60% sequence identity to SEQ ID NO: 2 and/or 4. The invention also relates to variants obtained by such method.

The invention further relates to compositions such as cleaning and detergent compositions and to the use of such compositions and variants of the present invention in cleaning processes such as laundry and/or dish wash.

Definitions

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J.

Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively.

Protease activity: The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below. The subtilisin variants of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 2 or 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a prokaryotic or eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent or compared to a protease with SEQ ID NO: 2, or compared to a protease having the identical amino acid sequence of said variant but not having the alterations at one or more of said specified positions. Such improved properties include, but are not limited to wash performance, protease activity, thermal activity profile, thermostability, pH activity profile, pH stability, substrate/cofactor specificity, improved surface properties, substrate specificity, product specificity, increased stability e.g. chelator stability or solubility in the presence of pretreated biomass, improved stability under storage conditions, and chemical stability.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants better able to catalyze a reaction in the presence of such chemicals. In a particular aspect of the invention the improved chemical stability is an improved stability in a detergent, in particular in a liquid detergent. The improved detergent stability is in particular an improved stability of the alpha amylase activity when an alpha amylase variant of the present invention is mixed into a liquid detergent formulation comprising a chelating agent, the liquid also includes gels or a paste. The liquid detergent formulation may refer to concentrated detergent which is added during a laundry or automated dish wash process or a dilute detergent such as a wash solution, i.e. an aqueous solution to which the concentrated detergent is added.

In the present invention, liquid detergents are particular useful as liquid laundry detergents.

Stability: The term "stability" includes storage stability and stability during use, e.g. during a wash process and reflects the stability of the protease as a function of time e.g. how much activity is retained when the protease is kept in solution in particular in a detergent solution. The stability is influenced by many factors e.g. pH, temperature, detergent composition e.g. amount of builder, surfactants etc.

Improved wash performance: The term "improved wash performance" is defined herein as a protease variant displaying an alteration of the wash performance of a protease variant relative to the wash performance of the parent subtilisin variant, relative to a protease with SEQ ID NO: 2 or relative to a protease having the identical amino acid sequence of said variant but not having the alterations at one or more of said specified positions e.g. by increased stain removal. The term "wash performance" includes wash performance in laundry but also e.g. in dish wash. The wash performance may be quantified by calculating the so-called intensity value (Int) defined in the description of Automatic Mechanical Stress Assay (AMSA) under the section "Material and Methods".

Improved protease activity: The term "improved protease activity" is defined herein as an altered protease activity (as defined above) of a protease variant displaying an alteration of the activity relative (or compared) to the activity of the parent protease, or compared to a protease with SEQ ID NO: 2, or relative to a protease having the identical amino acid sequence of said variant but not having the alterations at one or more of said specified positions, by increased protein conversion.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide corresponds to the amino acid sequence with SEQ ID NO: 2 or SEQ ID NO: 4.

Mature polypeptide coding sequence: The term "mature polypeptide coding sequence" means a polynucleotide that encodes a mature polypeptide having protease activity. In one aspect, the mature polypeptide coding sequence is nucleotides 322 to 1146 of SEQ ID NO: 1 based on the SignalP (Nielsen et al., 1997, Protein Engineering 10: 1-6)] that predicts nucleotides 1 to 91 of SEQ ID NO: 1 encodes a signal peptide.

In one aspect, the mature polypeptide coding sequence is nucleotides 577 to 1140 of SEQ ID NO: 3 based on the SignalP (Nielsen et al., 1997, Protein Engineering 10: 1-6)] that predicts nucleotides 1 to 81 of SEQ ID NO: 3 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide, such that the control sequence directs the expression of the coding sequence.

Parent: The term "parent" means a protease to which an alteration is made to produce the enzyme variants of the present invention. Thus the parent is a protease having the identical amino acid sequence of said variant but not having the alterations at one or more e.g. two or more of said specified positions. It will be understood, that in the present context the expression "having identical amino acid sequence" relates to 100% sequence identity. The parent may be a naturally occurring (wild-type) polypeptide or a variant thereof. In a particular embodiment the parent is a protease with at least 60% identity, such as at least 65%, at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% identity to a polypeptide with SEQ ID NO: 2 or 4.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

The length of the alignment is preferably at least 150 amino acid residues, at least 175 amino acid residues, at least 200 amino acid residues, at least 220 amino acid residues, at least 240 amino acid residues or at least 260 amino acid residues.

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

The length of the alignment is preferably at least 450 nucleotides, at least 525 nucleotides, at least 600 nucleotides, at least 660 nucleotides, at least 720 nucleotides or at least 840 nucleotides.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Variant: The term "variant" means a polypeptide having protease activity comprising an alteration, i.e., a substitution, insertion, and/or deletion, at one or more (or one or several) positions compared to its parent which is a protease having the identical amino acid sequence of said variant but not having the alterations at one or more of said specified positions. A substitution means a replacement of an amino acid occupying a position with a different amino acid; a deletion means removal of an amino acid occupying a position; and an insertion means adding amino acids e.g. 1 to 10 amino acids, such as 9 amino acids, such as 8 amino acids, such as 7 amino acids, such as 6 amino acids, such as 5 amino acids, such as 4 amino acids, preferably 1-3 amino acids, more preferably 1-2 amino acids and most preferably two amino acids adjacent to an amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wash performance: The term "wash performance" is used as an enzyme's ability to remove stains present on the object to be cleaned during e.g. wash, such as laundry or hard surface cleaning. The improvement in the wash performance may be quantified by calculating the so-called intensity value (Int) defined in AMSA assay as described in Materials and methods herein. See also the wash performance test in Example 2 herein.

Wild-Type protease: The term "wild-type protease" means a protease expressed by a naturally occurring organism, such as a bacterium, archaea, yeast, fungus, plant or animal found in nature. An example of a wild-type protease is BPN' (SEQ ID NO: 2) or Savinase (SEQ ID NO: 4).

Transcription promoter: The term "transcription promoter" is used for a promoter which is a region of DNA that facilitates the transcription of a particular gene. Transcription promoters are typically located near the genes they regulate, on the same strand and upstream (towards the 5' region of the sense strand).

Transcription terminator: The term "transcription terminator" is used for a section of the genetic sequence that marks the end of gene or operon on genomic DNA for transcription.

Conventions for Designation of Variants

For purposes of the present invention, the mature polypeptide disclosed in SEQ ID NO: 2 is used to determine the corresponding amino acid residue in another subtilisin. The amino acid sequence of another subtilisins is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another subtilisin can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+ S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases, the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Numbering of Amino Acid Positions/Residues

If nothing else is mentioned, the amino acid numbering used herein correspond to that of the subtilase BPN' (BASBPN) sequence. For further description of the BPN' sequence, see SEQ ID NO:2 or Siezen et al., Protein Engng. 4 (1991) 719-737.

In the following, the term "corresponding to" is to be understood as corresponding to a position of SEQ ID NO: 2, i.e. the numbering throughout the document is according to BPN'.

DETAILED DESCRIPTION OF THE INVENTION

The inventors have found that changing the overall charge of the positions corresponding to position 217 or 218 of SEQ ID NO: 2 resulted in variants with increased wash performance in particular on egg stains. Increasing either the positive or negative charge at both positions corresponding to position 217 and 218 of SEQ ID NO: 2 i.e. by substitution the amino acid occupying position 217 and the amino acid occupying position 218 with an amino acid which is either more negatively or more positively charged resulted in protease variants with improved properties compared to its parent e.g. compared to SEQ ID NO: 2. In particular, the variants according to the invention have increased wash performance compared to SEQ ID NO: 2, SEQ ID NO: 2 with the Y217L mutation or compared to a single charge change in either position 217 or 218. Though a single substitution at either position 217 or 218 with an amino acid more charged than the substituted amino acid may provide a beneficial effect on wash performance this effect was more pronounced when both the positions 217 and 218 were made more positively charged or more negatively charged compared to SEQ ID NO: 2 i.e. by substituting the amino acids corresponding to 217 and 218 of SEQ ID NO: 2 in the parent protease with either the negatively charged amino acids the amino acids D, E or the positively charged amino acids R, K and H. Increased performance was also seen when substitution with the polar amino acids S and T at positions corresponding to positions 217 and 218 of SEQ ID NO: 2. The inventors found that increased wash performance is obtained when the substitutions lead to an overall change in charge at the two positions corresponding to position 217 ad 218 of SEQ ID NO: 2. Thus variants with the same charge at position 217 and 218 e.g. a negative charge on both positions such as Y217E+N218D showed increased performance compared the parent, to a protease with SEQ ID NO: 2 or relative to a protease having the identical amino acid sequence of said variant but not having the alterations at one or more of said specified positions. Making the protease either more positive or more negative charged at positions corresponding to position 217 or 218 of SEQ ID NO: 2 results in protease variants which are more hydrophilic. Thus according to one embodiment the protease variants are more hydrophilic at the positions corresponding to positions 217 and 218 of SEQ ID NO: 2 compared the parent, to a protease with SEQ ID NO: 2 or relative to a protease having the identical amino acid sequence of said variant but not having the alterations at one or more of said specified positions.

Thus, one aspect of the invention relates to subtilisin variants comprising any of the substitutions corresponding to Y217D, Y217E, Y217R, Y217K, Y217H, Y217S, Y217T, Y218D, Y218E, Y218R, Y218K, Y218H, Y218S or Y218T of SEQ ID NO2. In a particular aspect the variant comprises any of the substitutions corresponding to Y217D, Y217E, Y217R, Y217K, Y217H, Y217S, Y217T, Y218D, Y218E, Y218R, Y218K, Y218H, Y218S or Y218T of SEQ ID NO 2 wherein the variant has at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, but less than 100%, sequence identity to the mature polypeptide of SEQ ID NO: 2 and/or 4.

Another aspect of the invention relates to subtilisin variants comprising the substitutions corresponding to Y217X and N218Z of SEQ ID NO: 2, wherein X and Z are selected from the group consisting of D, E, R, K, H, S and T, wherein when X is either D, E, S or T then Z is also selected from D, E, S or T and wherein when X is either K, H or R then Z is also selected from K, H or R. In a particular aspect X and Z are the same amino acid, in one aspect X and Z are the same and are selected from the group consisting of D, E, R, K, H, S and T. In a further aspect X and Z are D, E, S or T in yet an aspect X and Z is K, H or R. In a preferred aspect the invention relates to subtilisin variants comprising the substitutions corresponding to Y217X and N218Z of SEQ ID NO: 2, wherein X and Z are selected from the group consisting of D, E, R, K, H, S and T, wherein when X is either D, E, S or T then Z is also selected from D, E, S or T, wherein when X is either K, H or R then Z is also selected from K, H or R and wherein the variant has at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, but less than 100%, sequence identity to the mature polypeptide of SEQ ID NO: 2 or 4. In one embodiment the variant according to the invention is a polypeptide encoded by a polynucleotide having at least 60% identity to the mature polypeptide coding sequence of SEQ ID NO: 1 or 3 or a sequence encoding the mature polypeptide of SEQ ID NO: 2 or 4. In one embodiment the variant according the invention is a polypeptide encoded by a polynucleotide having at least 65% identity e.g., at least 70%, at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, but less than 100%, sequence identity to the mature polypeptide of SEQ ID NO: 1 or 3.

Another embodiment concerns a method for obtaining a variant of a subtilisin parent protease, comprising introducing into a parent subtilisin the substitutions corresponding to Y217X and N218Z of SEQ ID NO 2, wherein X and Z are selected from the group consisting of K, H, R, D, E, S and T, wherein when X is either D, E, S or T then Z is also selected from D, E, S or T and wherein when X is either K, H or R then Z is also selected from K, H or R; recovering the variant and testing if said variant has protease activity. A particular aspect concerns a method for obtaining a variant of a subtilisin parent protease, comprising introducing into a parent subtilisin the substitutions corresponding to Y217X and N218Z of SEQ ID NO 2, wherein X and Z are selected from the group consisting of K, H, R, D, E, S and T, wherein when X is either D, E, S or T then Z is also selected from D, E, S or T and wherein when X is either K, H or R then Z is also selected from K, H or R; recovering the variant and testing if said variant has protease activity, wherein the variant is a variant of a subtilisin parent protease selected from the group consisting of:

a. a polypeptide having at least 60% sequence identity to the mature polypeptide of SEQ ID NO: 2 or 4;

b. a polypeptide encoded by a polynucleotide that hybridizes under low stringency conditions with (i) the mature polypeptide coding sequence of SEQ ID NO: 1 or 3, (ii) the cDNA sequence thereof, or (iii) the full-length complement of (i) or (ii);

c. a polypeptide encoded by a polynucleotide having at least 60% identity to the mature polypeptide coding sequence of SEQ ID NO: 1 or 3, or the cDNA sequence thereof; and d. a fragment of the mature polypeptide of SEQ ID NO: 2 or 4, which has protease activity.

A particular embodiment, concerns a method for obtaining a variant of a subtilisin parent protease, comprising introducing into a parent subtilisin the substitutions corresponding to Y217X and N218Z of SEQ ID NO: 2, wherein X and Z are selected from the group consisting of K, H, R, D, E, S and T, wherein when X is either D, E, S or T then Z is also selected from D, E, S or T, wherein when X is either K, H or R then Z is also selected from K, H or R and wherein the variant is a variant of a parent subtilisin having at least 60%, such as at least 65%, e.g., at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, or 100% sequence identity to the mature polypeptide of SEQ ID NO: 2 or 4. In one embodiment, the protease variant is a BPN' (SEQ ID NO: 2) variant comprising the substitutions corresponding to Y217X and N218Z of SEQ ID NO: 2, wherein X and Z are selected from the group consisting of D, E, R, K, H, S and T. In another embodiment the invention relates a BPN' variant comprising any of the substitutions selected from the group consisting of [Y217D+N218D], [Y217E+N218E], [Y217D+N218E], [Y217E+N218D], [Y217E+N218S], [Y217S+N218E], [Y217S+N218S], [Y217D+N218S], [Y217S+N218D], [Y217E+N218T], [Y217T+N218E], [Y217T+N218T], [Y217D+N218T], [Y217T+N218D] [Y217K+N218K], [Y217R+N218R], [Y217K+N218R], [Y217R+N218K], [Y217R+N218H], [Y217H+N218R], [Y217H+N218H], [Y217K+N218H], [Y217H+N218K]. In yet another embodiment the invention relates a BPN' variant comprising any of the substitutions selected from the group consisting of [Y217D+N218D], [Y217E+N218E], [Y217D+N218E], [Y217E+N218D], [Y217E+N218S], [Y217S+N218E], [Y217S+N218S], [Y217D+N218S], [Y217S+N218D], [Y217E+N218T], [Y217T+N218E], [Y217T+N218T], [Y217D+N218T], [Y217T+N218D] [Y217K+N218K], [Y217R+N218R], [Y217K+N218R], [Y217R+N218K], [Y217R+N218H], [Y217H+N218R], [Y217H+N218H], [Y217K+N218H], [Y217H+N218K], wherein the variant has at least 65%, such as at least 70%, e.g., at least 75%, at least 76% at least 77% at least 78% at least 79% at least 80%, at least 81% at least 82% at least 83% at least 84% at least 85%, at least 86%, at least 87% at least 88% at least 89%, at least 90%, at least 91%, at least 92%, at least 93%, at least 94% at least 95% identity, at least 96%, at least 97%, at least 98%, or at least 99%, but less than 100%, sequence identity to the mature polypeptide of SEQ ID NO: 2.

In another particular embodiment, the protease variant is a Savinase (SEQ ID NO: 4) variant comprising the substitutions corresponding to L217X and N218Z of SEQ ID NO: 2, wherein X and Z are selected from the group consisting of D, E, R, K, H, S and T. In another embodiment the invention relates a Savinase variant comprising any of the substitutions selected from the group consisting of [L217D+N218D], [L217E+N218E], [L217D+N218E], [L217E+N218D], [L217E+N218S], [L217S+N218E], [L217S+N218S], [L217D+N218S], [L217S+N218D], [L217E+N218T], [L217T+N218E], [L217T+N218T], [L217D+N218T], [L217T+N218D] [L217K+N218K], [L217R+N218R], [L217K+N218R], [L217R+N218K], [L217R+N218H], [L217H+N218R], [L217H+N218H], [L217K+N218H], [L217H+N218K]. In yet another embodiment, the invention relates a Savinase variant comprising any of the substitutions selected from the group consisting of [L217D+N218D], [L217E+N218E], [L217D+N218E], [L217E+N218D], [L217E+N218S], [L217S+N218E], [L217S+N218S], [L217D+N218S], [L217S+N218D], [L217E+N218T], [L217T+N218E], [L217T+N218T], [L217D+N218T], [L217T+N218D] [L217K+N218K], [L217R+N218R], [L217K+N218R], [L217R+N218K], [L217R+N218H], [L217H+N218R], [L217H+N218H], [L217K+N218H], [L217H+N218K], wherein the variant has at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, but less than 100%, sequence identity to the mature polypeptide of SEQ ID NO: 4.

In one embodiment, the variant comprises a substitution at a position corresponding to position 217 of SEQ ID NO: 2 with K and further comprises a substitution at a position corresponding to position 218 of SEQ ID NO: 2 with K.

In one embodiment, the variant comprises a substitution at a position corresponding to position 217 of SEQ ID NO: 2 with K and further comprises a substitution at a position corresponding to position 218 of SEQ ID NO: 2 with R.

In one embodiment, the variant comprises a substitution at a position corresponding to position 217 of SEQ ID NO: 2 with R and further comprises a substitution at a position corresponding to position 218 of SEQ ID NO: 2 with K.

In one embodiment, the variant comprises a substitution at a position corresponding to position 217 of SEQ ID NO: 2 with R and further comprises a substitution at a position corresponding to position 218 of SEQ ID NO: 2 with R.

In one embodiment, the variant comprises a substitution at a position corresponding to position 217 of SEQ ID NO: 2 with H and further comprises a substitution at a position corresponding to position 218 of SEQ ID NO: 2 with R.

In one embodiment, the variant comprises a substitution at a position corresponding to position 217 of SEQ ID NO: 2 with R and further comprises a substitution at a position corresponding to position 218 of SEQ ID NO: 2 with H.

In one embodiment, the variant comprises a substitution at a position corresponding to position 217 of SEQ ID NO: 2 with H and further comprises a substitution at a position corresponding to position 218 of SEQ ID NO: 2 with K.

In one embodiment, the variant comprises a substitution at a position corresponding to position 217 of SEQ ID NO: 2 with K and further comprises a substitution at a position corresponding to position 218 of SEQ ID NO: 2 with H.

In one embodiment, the variant comprises a substitution at a position corresponding to position 217 of SEQ ID NO: 2 with H and further comprises a substitution at a position corresponding to position 218 of SEQ ID NO: 2 with H In one embodiment, the variant comprises a substitution at a position corresponding to position 217 of SEQ ID NO: 2 with D and further comprises a substitution at a position corresponding to position 218 of SEQ ID NO: 2 with D.

In one embodiment, the variant comprises a substitution at a position corresponding to position 217 of SEQ ID NO: 2 with E and further comprises a substitution at a position corresponding to position 218 of SEQ ID NO: 2 with D.

In one embodiment, the variant comprises a substitution at a position corresponding to position 217 of SEQ ID NO: 2 with D and further comprises a substitution at a position corresponding to position 218 of SEQ ID NO: 2 with E.

In one embodiment, the variant comprises a substitution at a position corresponding to position 217 of SEQ ID NO: 2 with E and further comprises a substitution at a position corresponding to position 218 of SEQ ID NO: 2 with E.

In one embodiment, the variant comprises a substitution at a position corresponding to position 217 of SEQ ID NO: 2 with E and further comprises a substitution at a position corresponding to position 218 of SEQ ID NO: 2 with S.

In one embodiment, the variant comprises a substitution at a position corresponding to position 217 of SEQ ID NO: 2 with S and further comprises a substitution at a position corresponding to position 218 of SEQ ID NO: 2 with E.

In one embodiment, the variant comprises a substitution at a position corresponding to position 217 of SEQ ID NO: 2 with D and further comprises a substitution at a position corresponding to position 218 of SEQ ID NO: 2 with S.

In one embodiment, the variant comprises a substitution at a position corresponding to position 217 of SEQ ID NO: 2 with S and further comprises a substitution at a position corresponding to position 218 of SEQ ID NO: 2 with D.

In one embodiment, the variant comprises a substitution at a position corresponding to position 217 of SEQ ID NO: 2 with S and further comprises a substitution at a position corresponding to position 218 of SEQ ID NO: 2 with S.

In one embodiment, the variant comprises a substitution at a position corresponding to position 217 of SEQ ID NO: 2 with E and further comprises a substitution at a position corresponding to position 218 of SEQ ID NO: 2 with T.

In one embodiment, the variant comprises a substitution at a position corresponding to position 217 of SEQ ID NO: 2 with T and further comprises a substitution at a position corresponding to position 218 of SEQ ID NO: 2 with E.

In one embodiment, the variant comprises a substitution at a position corresponding to position 217 of SEQ ID NO: 2 with D and further comprises a substitution at a position corresponding to position 218 of SEQ ID NO: 2 with T.

In one embodiment, the variant comprises a substitution at a position corresponding to position 217 of SEQ ID NO: 2 with T and further comprises a substitution at a position corresponding to position 218 of SEQ ID NO: 2 with D.

In one embodiment, the variant comprises a substitution at a position corresponding to position 217 of SEQ ID NO: 2 with T and further comprises a substitution at a position corresponding to position 218 of SEQ ID NO: 2 with T.

In one aspect, the total number of alterations in the variants of the present invention is 1-20, e.g., 1-10 and 1-5, such as 1, 2, 3, 4, 5, 6, 7, 8, 9 or 10 alterations.

In one aspect, the variant comprises or consists of an alteration at a position corresponding to position 217. In another aspect, the amino acid at a position corresponding to position 217 is substituted with Asp, Glu, Arg, Lys, Ser, Thr or His preferably with Asp. In another aspect, the variant comprises or consists of the substitution Y217D of the mature polypeptide of SEQ ID NO: 2.

In one aspect, the variant comprises or consists of an alteration at a position corresponding to position 218. In another aspect, the amino acid at a position corresponding to position 218 is substituted with Asp, Glu, Arg, Lys, Ser, Thr or His, preferably with Lys. In another aspect, the variant comprises or consists of the substitution N218K of the mature polypeptide of SEQ ID NO: 2.

In one aspect, the variant comprises or consists of an alteration at a position corresponding to position 217 and an alteration at a position corresponding position 218 wherein said position 217 and 218 are substituted with Asp, Glu, Arg, Lys, Ser, Thr or His. In another aspect, the variant comprises or consists of an alteration at a position corresponding to position 217 and an alteration at a position corresponding position 218, wherein said position 217 and 218 are substituted with Asp, Glu, Arg, Lys, Ser, Thr or His, and wherein the substitution at position 217 and 218 is with the same amino acid. Thus, in one aspect the variant comprises or consists of the substitutions Y217D+N218D, Y217E+N218E, Y217S+N218S, Y217T+N218T, Y217R+N218R, Y217H+N218H or Y217K+R218K. In another aspect, the variant comprises or consists of an alteration at a position corresponding to position 217 and an alteration at a position corresponding to position 218 of SEQ ID NO: 2 with Asp, Glu, Arg, Lys, Ser, Thr or His, wherein the substitution at position 217 and 218 is not with the same amino acid and wherein the substitution at position 217 and 218 result in an overall change of charge at these two positions. Thus in one aspect the variant comprises or consists of the substitutions Y217D+N218E, Y217E+N218D, Y217D+N218S, Y217S+N218D, Y217E+N218S, Y217S+N218E, Y217D+N218T, Y217T+N218D, Y217E+N218T, Y217T+N218E, Y217R+N218K, Y217K+N218R, Y217R+N218H, Y217H+N218R, Y217H+N218K or Y217K+R217H.

Thus, one aspect of the invention concerns subtilisin variant, comprising the substitutions corresponding to Y217X and N218Z of SEQ ID NO: 2, wherein X and Z are selected from the group consisting of D, E, R, K, H, S and T and wherein X and Z are the same amino acid.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are D.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are E.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are S.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are T.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are R.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are K.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are the same amino acid and wherein X and Z are H.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is D and Z is E.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is D and Z is S.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is D and Z is T.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is E and Z is D.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is E and Z is S.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is E and Z is T.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is T and Z is D.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is T and Z is E.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is T and Z is S One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is S and Z is D.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is S and Z is E.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is S and Z is T.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is K and Z is R.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is K and Z is H One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is R and Z is K.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is R and Z is H.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is H and Z is K.

One aspect of the invention concerns a subtilisin variant, comprising the substitutions corresponding to Y217X and N218Z of SEQ ID NO: 2, wherein X and Z are selected from the group consisting of D, E, R, K, H, S and T, wherein X and Z are not the same amino acid and wherein X is H and Z is R.

One aspect of the invention relates to a subtilisin variant, comprising the substitutions corresponding to Y217X and N218Z of SEQ ID NO: 2, wherein X and Z are selected from the group consisting of D, E, R, K, H, S and T and wherein X and Z is D, E, S or T.

One aspect of the invention relates to a subtilisin variant, comprising the substitutions corresponding to Y217X and N218Z of SEQ ID NO: 2, wherein X and Z are selected from the group consisting of D, E, R, K, H, S and T and wherein X and Z is R, K or H.

In another aspect, the variant comprises or consists of the substitutions L217D and N218D of the mature polypeptide of SEQ ID NO: 4.

In another aspect, the variant comprises or consists of the substitutions L217E and N218E of the mature polypeptide of SEQ ID NO: 4.

In another aspect, the variant comprises or consists of the substitutions L217S and N218S of the mature polypeptide of SEQ ID NO: 4.

In another aspect, the variant comprises or consists of the substitutions L217T and N218T of the mature polypeptide of SEQ ID NO: 4.

In another aspect, the variant comprises or consists of the substitutions L217D and N218E of the mature polypeptide of SEQ ID NO: 4.

In another aspect, the variant comprises or consists of the substitutions L217E and N218D of the mature polypeptide of SEQ ID NO: 4.

In another aspect, the variant comprises or consists of the substitutions L217D and N218S of the mature polypeptide of SEQ ID NO: 4.

In another aspect, the variant comprises or consists of the substitutions L217S and N218D of the mature polypeptide of SEQ ID NO: 4.

In another aspect, the variant comprises or consists of the substitutions L217S and N218E of the mature polypeptide of SEQ ID NO: 4.

In another aspect, the variant comprises or consists of the substitutions L217E and N218S of the mature polypeptide of SEQ ID NO: 4.

In another aspect, the variant comprises or consists of the substitutions L217D and N218T of the mature polypeptide of SEQ ID NO: 4.

In another aspect, the variant comprises or consists of the substitutions L217T and N218D of the mature polypeptide of SEQ ID NO: 4.

In another aspect, the variant comprises or consists of the substitutions L217E and N218T of the mature polypeptide of SEQ ID NO: 4.

In another aspect, the variant comprises or consists of the substitutions L217T and N218E of the mature polypeptide of SEQ ID NO: 4.

In another aspect, the variant comprises or consists of the substitutions L217K and N218K of the mature polypeptide of SEQ ID NO: 4.

In another aspect, the variant comprises or consists of the substitutions L217R and N218R of the mature polypeptide of SEQ ID NO: 4.

In another aspect, the variant comprises or consists of the substitutions L217H and N218H of the mature polypeptide of SEQ ID NO: 4.

In another aspect, the variant comprises or consists of the substitutions L217K and N218R of the mature polypeptide of SEQ ID NO: 4.

In another aspect, the variant comprises or consists of the substitutions L217K and N218H of the mature polypeptide of SEQ ID NO: 4.

In another aspect, the variant comprises or consists of the substitutions L217R and N218K of the mature polypeptide of SEQ ID NO: 4.

In another aspect, the variant comprises or consists of the substitutions L217R and N218H of the mature polypeptide of SEQ ID NO: 4.

In another aspect, the variant comprises or consists of the substitutions L217H and N218R of the mature polypeptide of SEQ ID NO: 4.

In another aspect, the variant comprises or consists of the substitutions L217H and N218K of the mature polypeptide of SEQ ID NO: 4.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Asn/Gln, Thr/Ser, Ala/Gly, Ala/Thr, Ser/Asn, Ala/Val, Ser/Gly, Tyr/Phe, Ala/Pro, Lys/Arg, Asp/Asn, Glu/Gln, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

For example, the variants may comprise an alteration at the positions corresponding to positions 217 and 218 and further comprise an alteration at another position(s) as long as the alteration does not affect the performance of the variant. Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. For BPN' (SEQ ID NO: 2) the catalytic triad comprising the amino acids S221, H64, and D32 is essential for protease activity of the enzyme.

The variants may consist of 200 to 900 amino acids, e.g., 210 to 800, 220 to 700, 230 to 600, 240 to 500, 250 to 400, 255 to 300, 260 to 290, 265 to 285, 270 to 280 or 270, 271, 272, 273, 274, 275, 276, 277, 278, 279 or 280 amino acids.

In an embodiment, the variant has improved catalytic activity compared to the parent enzyme.

In an embodiment, the variant has improved wash performance compared to the parent enzyme or compared to a protease having the identical amino acid sequence of said variant but not having the alterations at one or more of said specified positions or compared to a protease with SEQ ID NO 2, wherein wash performance is measured as described in example 2 in "Material and Methods" herein.

Parent Proteases

Enzymes cleaving the amide linkages in protein substrates are classified as proteases, or (interchangeably) peptidases (see Walsh, 1979, Enzymatic Reaction Mechanisms. W.H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) Bacteriological Rev. 41 711-753).

Subtilases

A sub-group of the serine proteases tentatively designated subtilases has been proposed by Siezen et al., Protein Engng. 4 (1991) 719-737 and Siezen et al. Protein Science 6 (1997) 501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN', subtilisin Carlsberg (ALCALASE®, NOVOZYMES A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Genencor International Inc.), subtilisin 309 (SAVINASE®, NOVOZYMES A/S), subtilisin 147 (BLS147) (ESPERASE®, NOVOZYMES A/S), and alkaline elastase YaB (BSEYAB). BPN' is subtilisin BPN' from *B. amyloliquefaciens* BPN' has the amino acid sequence SEQ ID NO 2.

Subtilisins

Subtilisins are serine proteases from the family S8, in particular from the subfamily S8A, as defined by the MEROPS database (http://merops.sangerac.uk/cgi-bin/famsum?family=S8). BPN' and Savinase have the MEROPS numbers S08.034 and S08.003, respectively.

Parent Subtilisin

The term "parent subtilisin" describes a subtilase defined according to Siezen et al. (1991 and 1997). For further details see description of "Subtilases" above. A parent subtilisin may also be a subtilase isolated from a natural source, wherein subsequent modifications have been made while retaining the characteristic of a subtilase. Furthermore, a parent subtilisin may be a subtilase which has been prepared by the DNA shuffling technique, such as described by J. E. Ness et al., Nature Biotechnology, 17, 893-896 (1999).

Alternatively, the term "parent subtilisin" may be termed "wild type subtilase".

For reference a table of the acronyms for various subtilases mentioned herein is provided, for further acronyms, see Siezen et al., Protein Engng. 4 (1991) 719-737 and Siezen et al. Protein Science 6 (1997) 501-523.

TABLE III

| Organism | enzyme | acronym |
|---|---|---|
| Bacteria: Gram-positive | | |
| *Bacillus subtilis* 168 | subtilisin I168,apr | BSS168 |
| *Bacillus amyloliquefaciens* | subtilisin BPN' (NOVO) | BASBPN |
| *Bacillus subtilis* DY | subtilisin DY | BSSDY |
| *Bacillus licheniformis* | subtilisin Carlsberg | BLSCAR |
| *Bacillus lentus* | subtilisin 309 | BLSAVI |
| *Bacillus lentus* | subtilisin 147 | BLS147 |
| *Bacillus alcalophilus* PB92 | subtilisin PB92 | BAPB92 |
| *Bacillus* YaB | alkaline elastase YaB | BYSYAB |
| *Bacillus* sp. NKS-21 | subtilisin ALP I | BSAPRQ |
| *Bacillus* sp. G-825-6 | subtilisin Sendai | BSAPRS |
| *Thermoactinomyces vulgaris* | thermitase | TVTHER |

Modification(s) of a Subtilase

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertion(s) in or at the amino acid(s) of interest.

Subtilisin Variant

The term "variant" and the term "subtilisin variant" are defined above.

Homologous Subtilase Sequences

The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous subtilases, which can be modified according to the invention.

Substantially homologous parent subtilisin variants may have one or more (several) amino acid substitutions, deletions and/or insertions, in the present context the term "one or more" is used interchangeably with the term "several". These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, EMBO J. 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

The parent subtilisin may comprise or consist of the amino acid sequence of SEQ ID NO: 2 or an allelic variant thereof; or a fragment thereof having protease activity. In one aspect, the parent subtilisin comprises or consists of the amino acid sequence of SEQ ID NO: 2.

The parent subtilisin may be (a) a polypeptide having at least 65% sequence identity to the mature polypeptide of SEQ ID NO: 2 or 4; (b) a polypeptide encoded by a polynucleotide that hybridizes under medium or high stringency conditions with (i) the mature polypeptide coding sequence of SEQ ID NO: 1 or 3, (ii) a sequence encoding the mature polypeptide of SEQ ID NO: 2 or 4, or (iii) the full-length complement of (i) or (ii); or (c) a polypeptide encoded by a polynucleotide having at least 60% sequence identity to the mature polypeptide coding sequence of SEQ ID NO: 1 or 3.

In an aspect, the parent has a sequence identity to the mature polypeptide of SEQ ID NO: 2 or 4 of at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99%, or 100%, which have protease activity. In one aspect, the amino acid sequence of the parent differs by no more than 10 amino acids, e.g., 1, 2, 3, 4, 5, 6, 7, 8, or 9, from the mature polypeptide of SEQ ID NO: 2 or 4. In one preferred aspect, the amino acid sequence of the parent differs by no more than 10 amino acids, e.g., 1, 2, 3, 4, 5, 6, 7, 8, or 9, from the mature polypeptide of SEQ ID NO: 2 or 4 wherein the variants have retained its improved properties.

In another aspect, the parent comprises or consists of the amino acid sequence of SEQ ID NO: 2 or 4. In another aspect, the parent comprises or consists of the mature polypeptide of SEQ ID NO: 2 or 4. In another aspect, the parent comprises or consists of amino acids 1 to 275 of SEQ ID NO: 2. In yet another aspect, the parent comprises or consists of amino acids 1 to 269 of SEQ ID NO: 4.

In another aspect, the parent is encoded by a polynucleotide that hybridizes under very low stringency conditions, low stringency conditions, medium stringency conditions, or high stringency conditions, or very high stringency conditions with (i) the mature polypeptide coding sequence of SEQ ID NO: 1 or 3, (ii) a sequence encoding the mature polypeptide of SEQ ID NO: 2 or 4, or (iii) the full-length complement of (i) or (ii), (Sambrook et al., 1989, *Molecular Cloning, A Laboratory Manual*, 2d edition, Cold Spring Harbor, N.Y.).

The polynucleotide of SEQ ID NO: 1 or 3 or a subsequence thereof, as well as the polypeptide of SEQ ID NO: 2 or 4 or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or 3 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or 3; (ii) the mature polypeptide coding sequence of SEQ ID NO: 1 or 3; (iii) a sequence encoding the mature polypeptide of SEQ ID NO: 2 or 4; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or 3. In another aspect, the nucleotide acid probe is a 80 to 1140 nucleotides long fragment of SEQ ID NO: 1 or 3, e.g. 90, 100, 200, 300, 400, 500, 600, 700, 800, 900, 1000 or 1100 nucleotides long. In another aspect, the nucleic acid probe is a polynucleotide that encodes the polypeptide of SEQ ID NO: 2 or 4; the mature polypeptide thereof; or a fragment thereof. In another aspect, the nucleic acid probe is SEQ ID NO: 1 or 3 or a sequence encoding the mature polypeptide of SEQ ID NO: 2 or 4 respectively.

In another embodiment, the parent is encoded by a polynucleotide having a sequence identity to the mature polynucleotide coding sequence of SEQ ID NO: 1 or 3 of at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94% at least 95% identity, at least 96%, at least 97%, at least 98%, or at least 99% or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from organisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* protease, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* protease.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* protease In one aspect, the parent is a *Bacillus amyloliquefaciens* protease, e.g., the protease of SEQ ID NO: 2 or the mature polypeptide thereof.

In another aspect, the parent is a *Bacillus lentus* protease, e.g., the protease of SEQ ID NO: 4 or the mature polypeptide thereof.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method of obtaining a variant of a parent protease, comprising introducing into a parent protease the substitutions corresponding to Y217X and N218Z of SEQ ID NO: 2, wherein X and Z are selected from the group consisting of D, E, R, K, H, S and T; recovering the variant and testing if said variant has protease activity. The present invention further relates to a method of obtaining a variant of a parent protease, comprising introducing into a parent protease the substitutions corresponding to Y217X and N218Z of SEQ ID NO: 2, wherein X and Z are selected from the group consisting of D, E, R, K, H, S and T and wherein when X is selected from D, E, S, T then Z is also selected from D, E, S, T and when X is selected from R, K, H the Z is also selected from R, K, H; recovering the variant and testing if said variant has protease activity. Thus in a preferred aspect the present invention relates to a method of obtaining a variant of a parent protease, comprising introducing into a parent protease the substitutions corresponding to Y217X and N218Z of SEQ ID NO: 2, wherein X and Z are selected from the group consisting of D, E, S, T or R, K, H; recovering the variant and testing if said variant has protease activity. The invention further relates to method of obtaining a variant of a subtilisin parent protease, comprising introducing into a parent subtilisin the substitutions corresponding to Y217X and N218Z of SEQ ID NO: 2, wherein X and Z are selected from the group consisting of D, E, R, K, H, S and T; recovering the variant and testing if said variant has protease activity, wherein the parent subtilisin protease is selected from the group consisting of:

a. a polypeptide having at least 60% sequence identity to the mature polypeptide of SEQ ID NO: 2 or 4;
  b. a polypeptide encoded by a polynucleotide that hybridizes under low stringency conditions with (i) the mature polypeptide coding sequence of SEQ ID NO: 1 or 3, (ii) the cDNA sequence thereof, or (iii) the full-length complement of (i) or (ii);
  c. a polypeptide encoded by a polynucleotide having at least 60% identity to the mature polypeptide coding sequence of SEQ ID NO: 1 or 3, or the cDNA sequence thereof; and
  d. a fragment of the mature polypeptide of SEQ ID NO: 2 or 4, which has protease activity.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.*

16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

In one certain aspect, the variants according to the invention has improved wash performance compared to the parent enzyme or compared to a protease having the identical amino acid sequence of said variant but not having the alterations at one or more of said specified positions or compared to a protease with SEQ ID NO: 2, wherein wash performance is measure in AMSA as described in "Material and Methods" herein.

Thus, in a preferred embodiment the composition is a detergent composition, and one aspect of the invention relates to the use of a detergent composition comprising a variant according to the invention in a cleaning process such as laundry or hard surface cleaning.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Enzyme of the Present Invention

In one embodiment of the present invention, the variants of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708 or the variants according to the invention may be stabilized using peptide aldehydes or ketones such as described in WO 2005/105826 and WO 2009/118375.

A variant of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight of a cationic surfactant. Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof, Alkyl quaternary ammonium compounds, Alkoxylated quaternary ammonium (AQA), When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 1% to about 40% by weight of a zwitterionic surfactant. Non-limiting examples of zwitterionic surfactants include betaine, alkyldimethylbetaine, and sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash deteregent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may also contain 0-65% by weight, such as about 5% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-10% by weight, such as about 1% to about 5%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By bleach activator is meant herein a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetyl athylene diamine (TAED), sodium 3,5,5 trimethyl hexanoyloxybenzene sulphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy)benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore acethyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino) percapronic acid (PAP). The bleaching system may also include a bleach catalyst. In some embodiments the bleach component may be an organic catalyst selected from the group consisting of organic catalysts having the following formulae:

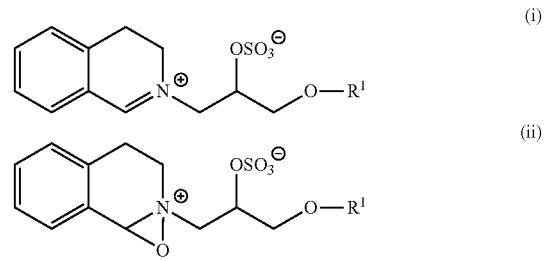

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259, WO 2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and poly-oxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments.

Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

(Additional) Enzymes

In one embodiment, the variants according to the invention are combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more additional enzymes such as carbohydrate-active enzymes like carbohydrase, pectinase, mannanase, amylase, cellulase, arabinase, galactanase, xylanase, or protease, lipase, a, cutinase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases:

The additional enzyme may be another protease or protease variant. The protease may be of animal, vegetable or microbial origin, including chemically or genetically modified mutants. Microbial origin is preferred. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect of the invention the additional protease may be a subtilase, such as a subtilisin or a variant hereof.

Examples of subtilisins are those derived from *Bacillus* such as subtilisin *lentus, Bacillus lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. Further examples of subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of trypsin-like proteases are trypsin (e.g. of porcine or bovine origin) and the *Fusarium* protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993.

Preferred commercially available protease enzymes include Alcalase™, Coronase™, Duralase™, Durazym™, Esperase™, Everlase™, Kannase™, Liquanase™, Liquanase Ultra™, Ovozyme™, Polarzyme™, Primase™, Relase™, Savinase and Savinase Ultra™, (Novozymes A/S), Axapem™ (Gist-Brocases N.V.), Excellase™, FN2™, FN3™, FN4™, Maxaca™, Maxapem™, Maxatase™, Properase™, Purafast™, Purafect™, Purafect OxP™, Purafect Prime™ and Puramax™ (DuPont/Genencor int.).

Lipases and Cutinases:

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g. *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluo-*

*rescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO2007/087508 and WO 2009/109500.

Preferred commercially available lipase enzymes include Lipolase™, Lipolase Ultra™, and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp lipase from Solvay.

Amylases:

Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent—

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1.,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl)disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers—

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

Formulation of Detergent Products

The detergent composition of the invention may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830,

WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,
WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,
WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Methods and Uses

The present invention is also directed to methods for using the variants according to the invention or compositions thereof in laundry of textile and fabrics, such as house hold laundry washing and industrial laundry washing.

The invention is also directed to methods for using the variants according to the invention or compositions thereof in hard surface cleaning such as automated Dish Washing (ADW), car wash and cleaning of Industrial surfaces.

The subtilisin variants of the present invention may be added to and thus become a component of a detergent composition. Thus one aspect of the invention relates to the use of a subtilisin variant, comprising the substitutions corresponding to Y217X and N218Z of SEQ ID NO: 2, wherein X and Z are selected from the groups consisting of R, K, H, or D, E, S, T and wherein the variant has at least 60% identity to SEQ ID NO: 2 or 4 in a cleaning process such as laundry and/or hard surface cleaning. Another aspect relates to the use of a detergent composition comprising subtilisin variant, comprising the substitutions corresponding to Y217X and N218Z of SEQ ID NO: 2, wherein X and Z are selected from the groups consisting of R, K, H, or D, E, S, T wherein the variant has a sequence identity to SEQ ID NO: 2 or 4 of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, at least 98%, or at least 99%, but less than 100%, sequence identity to the mature polypeptide of SEQ ID NO: 2 or 4.

One embodiment of the inventions relates to the use of a of a subtilisin variant, comprising the substitutions corresponding to Y217X and N218Z of SEQ ID NO: 2, wherein X and Z are selected from the groups consisting of R, K, H, or D, E, S, T and wherein the variant has at least 60% identity to SEQ ID NO: 2 or 4, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, at least 98%, or at least 99%, but less than 100%, sequence identity to the mature polypeptide of SEQ ID NO: 2 or 4 in a cleaning process such as laundry and/or hard surface cleaning, wherein the variant has increased wash performance relative to the parent or relative to a protease parent having the identical amino acid sequence of said variant but not having the substitutions at one or more of said positions when tested in example 2, as described under "Material and Methods".

A detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease variant of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and toweling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of protease variants of the invention in a proteinaceous stain removing processes. The proteinaceous stains may be stains such as food stains, e.g., baby food, sebum, cocoa, egg, blood, milk, ink, grass, or a combination hereof.

Typical detergent compositions include various components in addition to the enzymes, these components have different effects, some components like the surfactants lower the surface tension in the detergent, which allows the stain being cleaned to be lifted and dispersed and then washed away, other components like bleach systems remove discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a protease variant of the invention, wherein said enzyme composition further comprises at least one or more of the following: a surfactant, a builder, a chelator or chelating agent, bleach system or bleach component in laundry or dish wash.

In a preferred embodiment of the invention, the amount of a surfactant, a builder, a chelator or chelating agent, bleach system and/or bleach component are reduced compared to amount of surfactant, builder, chelator or chelating agent, bleach system and/or bleach component used without the added protease variant of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of a protease variant of the invention, such as a conventional amount of such component. In one aspect, a protease variant of the invention is used in detergent compositions wherein said composition is free of at least one component which is a surfactant, a builder, a chelator or chelating agent, bleach system or bleach component and/or polymer.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH from about 5.0 to about 11.5, or from about 6 to about 10.5, about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, about 8 to about 11, about 8 to about 10, about 8 to about 9, about 9 to about 11, about 9 to about 10, about 10 to about 11, preferably about 5.5 to about 11.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 16° dH, under typical US wash conditions about 6° dH, and under typical Asian wash conditions, about 3° dH.

The present invention relates to a method of cleaning a fabric, a dishware or hard surface with a detergent composition comprising a protease variant of the invention.

A preferred embodiment concerns a method of cleaning, said method comprising the steps of: contacting an object with a cleaning composition comprising a protease variant of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a protease of the invention under conditions suitable for cleaning said object.

In a preferred embodiment, the compositions for use in the methods above further comprise at least one additional enzyme as set forth in the "other enzymes" section above, such as an enzyme selected from the group of hydrolases such as proteases, lipases and cutinases, carbohydrases such as amylases, cellulases, hemicellulases, xylanases, and pectinase or a combination hereof. In yet another preferred embodiment the compositions for use in the methods above comprises a reduced amount of at least one or more of the following components a surfactant, a builder, a chelator or chelating agent, bleach system or bleach component or a polymer.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

In one embodiment, the protease variant is applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The protease variant can be applied to remove these sizing protein or protein derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme.

All issues, subject matter and embodiments which are disclosed for protease variants in this application are also applicable for methods and uses described herein. Therefore, it is explicitly referred to said disclosure for the methods and uses described herein as well.

The present invention is further described by the following examples that should not be construed as limiting the scope of the invention.

EXAMPLES

Materials and Methods

General Molecular Biology Methods

Unless otherwise mentioned the DNA manipulations and transformations were performed using standard methods of molecular biology (Sambrook et al. (1989); Ausubel et al. (1995); Harwood and Cutting (1990)).
Protease Assays:
1) Suc-AAPF-pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH. 20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.
2) Protazyme AK Assay:
Substrate: Protazyme AK tablet (cross-linked and dyed casein; from Megazyme)
Temperature: 37° C. (or set to other assay temperature).
Assay buffer: 100 mM succinic acid, 100 mM HEPES, 100 mM CHES, 100 mM CABS, 1 mM $CaCl_2$, 150 mM KCl, 0.01% Triton X-100, pH 6.5 or pH 7.0.
A Protazyme AK tablet was suspended in 2.0 ml 0.01% Triton X-100 by gentle stirring. 500 µl of this suspension and 500 µl assay buffer were dispensed in a microcentrifuge tube and placed on ice. 20 µl protease solution (diluted in 0.01% Triton X-100) was added to the ice-cold mixture. The assay was initiated by transferring the tube to a thermomixer at 37° C. and shaking at its highest rate (1400 rpm.). After 15 minutes the tube was put back into the ice bath. To remove unreacted substrate, the mixture was centrifuged in an ice cold centrifuge for a few minutes and 200 µl supernatant was transferred to a microtiter plate. The absorbance of the supernatant at 650 nm was measured. A sample with 20 µl of 0.01% Triton X-100 instead of protease solution was assayed in parallel, and its value was subtracted from the protease sample measurement.
Automatic Mechanical Stress Assay (AMSA) for Laundry In order to assess the wash performance in laundry, washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" on pages 23-24.

The laundry experiments are conducted under the experimental conditions specified below:

| | |
|---|---|
| Detergent dosage | 5 g/L (liquid detergent) |
| | 2.5 g/L (powder detergent) |
| Test solution volume | 160 micro L |
| pH | As is |
| Wash time | 20 minutes |
| Temperature | 30° C. |
| Water hardness | 15°dH |

Model detergents and test materials were as follows:

| | |
|---|---|
| Laundry liquid model detergent | Sodium alkylethoxy sulphate (C-9-15, 2EO) 6.0% |
| | Sodium dodecyl benzene sulphonate 3.0% |
| | Sodium toluene sulphonate 3.0% |
| | Olic acid 2.0% |
| | Primary alcohol ethoxylate (C12-15, 7EO) 3.0% |
| | Primary alcohol ethoxylate (C12-15, 3EO) 2.5% |
| | Ethanol 0.5% |
| | Monopropylene glycol 2.0% |
| | Tri-sodium citrate 2H2O 4.0% |
| | Triethanolamine 0.4% |
| | De-ionized water ad 100% |
| | pH adjusted to 8.5 with NaOH |
| Laundry powder model detergent | Sodium citrate dehydrate 32.3% |
| | Sodium-LAS 24.2% |
| | Sodium lauryl sulfate 32.2% |
| | Neodol 25-7 (alcohol ethoxylate) 6.4% |
| | Sodium sulfate 4.9% |
| Test material | PC-S-37 (whole egg on cotton/polyester) |
| | PC-S-39 (aged full egg on cotton/polyester) |

Water hardness was adjusted to 15° dH by addition of $CaCl_2$, $MgCl_2$, and $NaHCO_3$ ($Ca^{2+}$:$Mg^{2+}$=4:1:7.5) to the test system. After washing the textiles were flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}.$$

Example 1: Preparation and Testing of Protease Variants

Preparation and Expression of Variants

Mutation and introduction of an expression cassette into *Bacillus subtilis*.

All DNA manipulations were done by PCR (e.g. Sambrook et al.; Molecular Cloning; Cold Spring Harbor Laboratory Press) and can be repeated by everybody skilled in the art. Recombinant *B. subtilis* constructs encoding protease variants were used to inoculate shakeflasks containing a rich media (e.g. PS-1: 100 g/L Sucrose (Danisco cat. no. 109-0429), 40 g/L crust soy (soy bean flour), 10 g/L $Na_2HPO_4.12H_2O$ (Merck cat. no. 6579), 0.1 ml/L Pluronic PE 6100 (BASF 102-3098)). Cultivation typically takes 4 days at 30° C. shaking with 220 rpm.

Fermentation of Variants

Fermentation may be performed by methods well known in the art or as follows. A *B. subtilis* strain harboring the relevant expression plasmid was streaked on a LB-agar plate with a relevant antibiotic (6 µg/ml chloramphenicol), and grown overnight at 37° C.

The colonies were transferred to 100 ml PS-1 media supplemented with the relevant antibiotic in a 500 ml shaking flask.

Cells and other undissolved material were removed from the fermentation broth by centrifugation at 4500 rpm for 20-25 minutes. Afterwards the supernatant was filtered to obtain a clear solution.

Example 2: Testing Subtilisin Variants

The wash performance of the protease variants relative to BPN' (SEQ ID NO: 2) with the Y217L mutation were tested in a powder and a liquid model detergent at a temperature of 30° C. using the AMSA method as described under "Material and Methods".

Results:

The relative wash performance of the protease variants and their corresponding protease parent (SEQ ID NO: 2) with the Y217L for two stains PC-S-37 (whole egg on cotton/polyester) and PC-S-39 (Aged full egg on cotton/polyester) are shown in Table 2.1 below.

TABLE 2.1

| | AMSA data | | |
|---|---|---|---|
| | Stain | | |
| | PC-S-37 | | PC-S-39 |
| | Det 5 | PDET 2 | PDET 2 |
| Y217L | 100% | 100% | 100% |
| Y217E | 109% | 283% | 133% |
| Y217D | 438% | 700% | 267% |
| Y217R | 120% | 436% | 144% |
| N218E | 648% | 200% | 630% |
| N218D | 335% | 432% | 170% |
| N218S | 631% | — | 830% |
| N218T | 352% | 308% | 520% |

TABLE 2.1-continued

| | AMSA data | | |
|---|---|---|---|
| | Stain | | |
| | PC-S-37 | | PC-S-39 |
| | Det 5 | PDET 2 | PDET 2 |
| Y217E N218D | 949% | 693% | 1348% |
| Y217E N218E | 792% | 731% | 1754% |
| Y217K N218K | 582% | 1001% | 160% |
| Y217R N218R | 698% | 634% | 200% |
| Y217R N218K | 569% | 912% | 144% |
| Y217K N218R | 655% | 859% | — |
| Y217E N218S | 448% | 660% | 827% |
| Y217E N218T | 137% | 511% | — |
| Y217D N218S | 796% | 732% | 2069% |
| Y217D N218R | 10% | 318% | 213% |
| Y217E N218K | 2% | 148% | 8% |

The results show that a negative or positive charge at position 217 or 218, which can be provided by residue D, E, R or K, increases performance compared to a variant with no charge at one of these positions i.e. Y217L. Further, inserting one of the polar amino acids S or T also increased wash performance.

The effect of a negative charge at position 217 or 218 can be further increased by offering a second negative charge which could either the same amino acid or another charged amino acid i.e. either D or E as an example Y217E+N218D and Y217E+N218E compared to the corresponding single mutation variants Y217E, N218D and N218E in the same detergent.

Further, a positive charge at position 217 or 218 provided by residues K, H or R, increases performance. This effect could be enhanced by two positive charges at position 217 and 218 respectively i.e. Y217R+N218R, Y217K+N218R and Y217R+N218K have increased performance compared to variants with a single charge e.g. Y217R.

Variants with two positive charges or two negative charges at positions 217 and 218 were better than variants that combined a negative with a positive charge (Y217D+N218R, Y217E+N218K).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A subtilisin variant having protease activity comprising the substitutions corresponding to Y217X and N218Z of SEQ ID NO 2, wherein X and Z are the same and are either K or R, wherein the variant has at least 80% but less than 100% sequence identity to the mature polypeptide of SEQ ID NO: 2 and has an improved wash performance on egg stains compared to the mature polypeptide of SEQ ID NO: 2.

2. The subtilisin variant of claim 1, which has at least 85% sequence identity to the mature polypeptide of SEQ ID NO: 2.

3. The subtilisin variant of claim 1, which has at least 90% sequence identity to the mature polypeptide of SEQ ID NO: 2.

4. The subtilisin variant of claim 1, which has at least 95% sequence identity to the mature polypeptide of SEQ ID NO: 2.

5. The subtilisin variant of claim 1, which has at least 96% sequence identity to the mature polypeptide of SEQ ID NO: 2.

6. The subtilisin variant of claim 1, which has at least 97% sequence identity to the mature polypeptide of SEQ ID NO: 2.

7. The subtilisin variant of claim 1, which has at least 98% sequence identity to the mature polypeptide of SEQ ID NO: 2.

8. The subtilisin variant of claim 1, which has at least 99% sequence identity to the mature polypeptide of SEQ ID NO: 2.

9. The subtilisin variant of claim 1, which is a variant of the mature polypeptide of SEQ ID NO: 2.

10. The variant of claim 3, wherein X and Z are K.

11. The variant of claim 3, wherein X and Z are R.

12. The variant of claim 9, wherein X and Z are K.

13. The variant of claim 9, wherein X and Z are R.

14. The variant of claim 1, wherein the number of alterations is 2-20.

15. The variant of claim 1, wherein the number of alterations is 2-10.

16. The variant of claim 12, wherein the number of alterations is 2-10.

17. The variant of claim 13, wherein the number of alterations is 2-10.

18. A detergent composition comprising the variant of claim 1 and a surfactant.

19. A detergent composition comprising the variant of claim 4 and a surfactant.

\* \* \* \* \*

SEQUENCE LISTING

```
<160> NUMBER OF SEQ ID NOS: 4

<210> SEQ ID NO 1
<211> LENGTH: 1149
<212> TYPE: DNA
<213> ORGANISM: Bacillus amyloliquefaciens
<220> FEATURE:
<221> NAME/KEY: CDS
<222> LOCATION: (1)..(1146)
<220> FEATURE:
<221> NAME/KEY: sig_peptide
<222> LOCATION: (1)..(90)
```

```
<220> FEATURE:
<221> NAME/KEY: mat_peptide
<222> LOCATION: (322)..(1146)

<400> SEQUENCE: 1 atg aga ggc aaa aaa gta tgg atc agt ttg ctg ttt gct tta gcg tta      48
Met Arg Gly Lys Lys Val Trp Ile Ser Leu Leu Phe Ala Leu Ala Leu
    -105                -100                -95 atc ttt acg atg gcg ttc ggc agc aca tcc tct gcc cag gcg gca ggg      96
Ile Phe Thr Met Ala Phe Gly Ser Thr Ser Ser Ala Gln Ala Ala Gly
            -90                 -85                 -80 aaa tca aac ggg gaa aag aaa tat att gtc ggg ttt aaa cag aca atg     144
Lys Ser Asn Gly Glu Lys Lys Tyr Ile Val Gly Phe Lys Gln Thr Met
-75                 -70                 -65                 -60 agc acg atg agc gcc gct aag aag aaa gat gtc att tct gaa aaa ggc     192
Ser Thr Met Ser Ala Ala Lys Lys Lys Asp Val Ile Ser Glu Lys Gly
                -55                 -50                 -45 ggg aaa gtg caa aag caa ttc aaa tat gta gac gca gct tca gct aca     240
Gly Lys Val Gln Lys Gln Phe Lys Tyr Val Asp Ala Ala Ser Ala Thr
            -40                 -35                 -30 tta aac gaa aaa gct gta aaa gaa ttg aaa aaa gac ccg agc gtc gct     288
Leu Asn Glu Lys Ala Val Lys Glu Leu Lys Lys Asp Pro Ser Val Ala
-25                 -20                 -15 tac gtt gaa gaa gat cac gta gca cat gcg tac gcg cag tcc gtg cct     336
Tyr Val Glu Glu Asp His Val Ala His Ala Tyr Ala Gln Ser Val Pro
        -10                 -5                  -1   1              5 tac ggc gta tca caa att aaa gcc cct gct ctg cac tct caa ggc tac     384
Tyr Gly Val Ser Gln Ile Lys Ala Pro Ala Leu His Ser Gln Gly Tyr
                    10                  15                  20 act gga tca aat gtt aaa gta gcg gtt atc gac agc ggt atc gat tct     432
Thr Gly Ser Asn Val Lys Val Ala Val Ile Asp Ser Gly Ile Asp Ser
                25                  30                  35 tct cat cct gat tta aag gta gca ggc gga gcc agc atg gtt cct tct     480
Ser His Pro Asp Leu Lys Val Ala Gly Gly Ala Ser Met Val Pro Ser
            40                  45                  50 gaa aca aat cct ttc caa gac aac aac tct cac gga act cac gtt gcc     528
Glu Thr Asn Pro Phe Gln Asp Asn Asn Ser His Gly Thr His Val Ala
55                  60                  65 ggc aca gtt gcg gct ctt aat aac tca atc ggt gta tta ggc gtt gcg     576
Gly Thr Val Ala Ala Leu Asn Asn Ser Ile Gly Val Leu Gly Val Ala
        70                  75                  80                  85 cca agc gca tca ctt tac gct gta aaa gtt ctc ggt gct gac ggt tcc     624
Pro Ser Ala Ser Leu Tyr Ala Val Lys Val Leu Gly Ala Asp Gly Ser
                    90                  95                 100 ggc caa tac agc tgg atc att aac gga atc gag tgg gcg atc gca aac     672
Gly Gln Tyr Ser Trp Ile Ile Asn Gly Ile Glu Trp Ala Ile Ala Asn
                105                 110                 115 aat atg gac gtt att aac atg agc ctc ggc gga cct tct ggt tct gct     720
Asn Met Asp Val Ile Asn Met Ser Leu Gly Gly Pro Ser Gly Ser Ala
            120                 125                 130 gct tta aaa gcg gca gtt gat aaa gcc gtt gca tcc ggc gtc gta gtc     768
Ala Leu Lys Ala Ala Val Asp Lys Ala Val Ala Ser Gly Val Val Val
135                 140                 145 gtt gcg gca gcc ggt aac gaa ggc act tcc ggc agc tca agc aca gtg     816
Val Ala Ala Ala Gly Asn Glu Gly Thr Ser Gly Ser Ser Ser Thr Val
150                 155                 160                 165 ggc tac cct ggt aaa tac cct tct gtc att gca gta ggc gct gtt gac     864
Gly Tyr Pro Gly Lys Tyr Pro Ser Val Ile Ala Val Gly Ala Val Asp
            170                 175                 180 agc agc aac caa aga gca tct ttc tca agc gta gga cct gag ctt gat     912
Ser Ser Asn Gln Arg Ala Ser Phe Ser Ser Val Gly Pro Glu Leu Asp
```

```
Ser Ser Asn Gln Arg Ala Ser Phe Ser Ser Val Gly Pro Glu Leu Asp
            185                 190                 195 gtc atg gca cct ggc gta tct atc caa agc acg ctt cct gga aac aaa       960
Val Met Ala Pro Gly Val Ser Ile Gln Ser Thr Leu Pro Gly Asn Lys
        200                 205                 210 tac ggg gcg tac aac ggt acg tca atg gca tct ccg cac gtt gcc gga      1008
Tyr Gly Ala Tyr Asn Gly Thr Ser Met Ala Ser Pro His Val Ala Gly
215                 220                 225 gcg gct gct ttg att ctt tct aag cac ccg aac tgg aca aac act caa      1056
Ala Ala Ala Leu Ile Leu Ser Lys His Pro Asn Trp Thr Asn Thr Gln
230                 235                 240                 245 gtc cgc agc agt tta gaa aac acc act aca aaa ctt ggt gat tct ttc      1104
Val Arg Ser Ser Leu Glu Asn Thr Thr Thr Lys Leu Gly Asp Ser Phe
                250                 255                 260 tac tat gga aaa ggg ctg atc aac gta cag gcg gca gct cag taa          1149
Tyr Tyr Gly Lys Gly Leu Ile Asn Val Gln Ala Ala Ala Gln
                265                 270                 275

<210> SEQ ID NO 2
<211> LENGTH: 382
<212> TYPE: PRT
<213> ORGANISM: Bacillus amyloliquefaciens

<400> SEQUENCE: 2

Met Arg Gly Lys Lys Val Trp Ile Ser Leu Leu Phe Ala Leu Ala Leu
    -105                -100                 -95

Ile Phe Thr Met Ala Phe Gly Ser Thr Ser Ser Ala Gln Ala Ala Gly
     -90                 -85                 -80

Lys Ser Asn Gly Glu Lys Lys Tyr Ile Val Gly Phe Lys Gln Thr Met
-75                  -70                 -65                  -60

Ser Thr Met Ser Ala Ala Lys Lys Lys Asp Val Ile Ser Glu Lys Gly
             -55                 -50                 -45

Gly Lys Val Gln Lys Gln Phe Lys Tyr Val Asp Ala Ala Ser Ala Thr
             -40                 -35                 -30

Leu Asn Glu Lys Ala Val Lys Glu Leu Lys Lys Asp Pro Ser Val Ala
     -25                 -20                 -15

Tyr Val Glu Glu Asp His Val Ala His Ala Tyr Ala Gln Ser Val Pro
    -10                  -5                  -1   1                5

Tyr Gly Val Ser Gln Ile Lys Ala Pro Ala Leu His Ser Gln Gly Tyr
                 10                  15                  20

Thr Gly Ser Asn Val Lys Val Ala Val Ile Asp Ser Gly Ile Asp Ser
             25                  30                  35

Ser His Pro Asp Leu Lys Val Ala Gly Gly Ala Ser Met Val Pro Ser
         40                  45                  50

Glu Thr Asn Pro Phe Gln Asp Asn Asn Ser His Gly Thr His Val Ala
55                  60                  65

Gly Thr Val Ala Ala Leu Asn Asn Ser Ile Gly Val Leu Gly Val Ala
70                  75                  80                  85

Pro Ser Ala Ser Leu Tyr Ala Val Lys Val Leu Gly Ala Asp Gly Ser
                 90                  95                 100

Gly Gln Tyr Ser Trp Ile Ile Asn Gly Ile Glu Trp Ala Ile Ala Asn
                105                 110                 115

Asn Met Asp Val Ile Asn Met Ser Leu Gly Gly Pro Ser Gly Ser Ala
            120                 125                 130

Ala Leu Lys Ala Ala Val Asp Lys Ala Val Ala Ser Gly Val Val Val
        135                 140                 145
```

```
Val Ala Ala Ala Gly Asn Glu Gly Thr Ser Gly Ser Ser Ser Thr Val
150                 155                 160                 165

Gly Tyr Pro Gly Lys Tyr Pro Ser Val Ile Ala Val Gly Ala Val Asp
                170                 175                 180

Ser Ser Asn Gln Arg Ala Ser Phe Ser Ser Val Gly Pro Glu Leu Asp
            185                 190                 195

Val Met Ala Pro Gly Val Ser Ile Gln Ser Thr Leu Pro Gly Asn Lys
        200                 205                 210

Tyr Gly Ala Tyr Asn Gly Thr Ser Met Ala Ser Pro His Val Ala Gly
215                 220                 225

Ala Ala Ala Leu Ile Leu Ser Lys His Pro Asn Trp Thr Asn Thr Gln
230                 235                 240                 245

Val Arg Ser Ser Leu Glu Asn Thr Thr Thr Lys Leu Gly Asp Ser Phe
                250                 255                 260

Tyr Tyr Gly Lys Gly Leu Ile Asn Val Gln Ala Ala Ala Gln
                265                 270                 275

<210> SEQ ID NO 3
<211> LENGTH: 1143
<212> TYPE: DNA
<213> ORGANISM: Bacillus lentus
<220> FEATURE:

```
             35                  40                  45
ttt gta cca ggg gaa ccg tcg act caa gat ggg aat ggg cat ggc acg      525
Phe Val Pro Gly Glu Pro Ser Thr Gln Asp Gly Asn Gly His Gly Thr
 50                  55                  60 cat gtg gcc ggg acg atc gct gct tta aac aat tcg att ggc gtt ctt      573
His Val Ala Gly Thr Ile Ala Ala Leu Asn Asn Ser Ile Gly Val Leu
 65                  70                  75                  80 ggc gta gct cct agc gct gag cta tac gct gtt aaa gtc cta ggg gcg      621
Gly Val Ala Pro Ser Ala Glu Leu Tyr Ala Val Lys Val Leu Gly Ala
                 85                  90                  95 agc ggt tca ggt tcg gtc agc tcg att gcc caa gga ttg gaa tgg gca      669
Ser Gly Ser Gly Ser Val Ser Ser Ile Ala Gln Gly Leu Glu Trp Ala
            100                 105                 110 ggg aac aat ggc atg cac gtt gct aat ttg agt tta gga agc cct tcg      717
Gly Asn Asn Gly Met His Val Ala Asn Leu Ser Leu Gly Ser Pro Ser
        115                 120                 125 cca agt gcc aca ctc gag caa gct gtt aat agc gcg act tct aga ggc      765
Pro Ser Ala Thr Leu Glu Gln Ala Val Asn Ser Ala Thr Ser Arg Gly
    130                 135                 140 gtt ctt gtt gta gcg gca tct ggg aat tca ggt gca ggc tca atc agc      813
Val Leu Val Val Ala Ala Ser Gly Asn Ser Gly Ala Gly Ser Ile Ser
145                 150                 155                 160 tat ccg gcg cgc tat gcg aac gca atg gca gtc gga gct act gat caa      861
Tyr Pro Ala Arg Tyr Ala Asn Ala Met Ala Val Gly Ala Thr Asp Gln
                165                 170                 175 aac aac aac cgc gct agc ttt tca cag tat ggc gca ggc ctt gac att      909
Asn Asn Asn Arg Ala Ser Phe Ser Gln Tyr Gly Ala Gly Leu Asp Ile
            180                 185                 190 gtc gca ccc ggg gta aac gtg cag agc aca tac cca ggt tca aca tat      957
Val Ala Pro Gly Val Asn Val Gln Ser Thr Tyr Pro Gly Ser Thr Tyr
        195                 200                 205 gcc agc tta aac ggt aca tcg atg gct act cct cat gtt gca ggt gcg     1005
Ala Ser Leu Asn Gly Thr Ser Met Ala Thr Pro His Val Ala Gly Ala
    210                 215                 220 gcc gcc ctt gtt aaa caa aag aac cca tct tgg tct aat gta caa att     1053
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg     1101
Arg Asn His Leu Lys Asn Thr Ala Thr Ser Leu Gly Ser Thr Asn Leu
                245                 250                 255 tat gga agc gga ctt gtt aac gca gaa gcg gca acg cgt taa            1143
Tyr Gly Ser Gly Leu Val Asn Ala Glu Ala Ala Thr Arg
            260                 265

<210> SEQ ID NO 4
<211> LENGTH: 380
<212> TYPE: PRT
<213> ORGANISM: Bacillus lentus

<400> SEQUENCE: 4

Met Lys Lys Pro Leu Gly Lys Ile Val Ala Ser Thr Ala Leu Leu
    -110                -105                -100

Ile Ser Val Ala Phe Ser Ser Ser Ile Ala Ser Ala Ala Glu Glu Ala
        -95                 -90                 -85

Lys Glu Lys Tyr Leu Ile Gly Phe Asn Glu Gln Glu Ala Val Ser Glu
-80                 -75                 -70                 -65

Phe Val Glu Gln Val Glu Ala Asn Asp Glu Val Ala Ile Leu Ser Glu
                -60                 -55                 -50

Glu Glu Glu Val Glu Ile Glu Leu Leu His Glu Phe Glu Thr Ile Pro
```

-continued

```
            -45             -40             -35
Val Leu Ser Val Glu Leu Ser Pro Glu Asp Val Asp Ala Leu Glu Leu
        -30             -25             -20

Asp Pro Ala Ile Ser Tyr Ile Glu Glu Asp Ala Glu Val Thr Thr Met
    -15             -10              -5              -1

Ala Gln Ser Val Pro Trp Gly Ile Ser Arg Val Gln Ala Pro Ala Ala
 1               5              10              15

His Asn Arg Gly Leu Thr Gly Ser Gly Val Lys Val Ala Val Leu Asp
            20              25              30

Thr Gly Ile Ser Thr His Pro Asp Leu Asn Ile Arg Gly Gly Ala Ser
            35              40              45

Phe Val Pro Gly Glu Pro Ser Thr Gln Asp Gly Asn Gly His Gly Thr
            50              55              60

His Val Ala Gly Thr Ile Ala Ala Leu Asn Asn Ser Ile Gly Val Leu
 65              70              75              80

Gly Val Ala Pro Ser Ala Glu Leu Tyr Ala Val Lys Val Leu Gly Ala
            85              90              95

Ser Gly Ser Gly Ser Val Ser Ser Ile Ala Gln Gly Leu Glu Trp Ala
            100             105             110

Gly Asn Asn Gly Met His Val Ala Asn Leu Ser Leu Gly Ser Pro Ser
            115             120             125

Pro Ser Ala Thr Leu Glu Gln Ala Val Asn Ser Ala Thr Ser Arg Gly
            130             135             140

Val Leu Val Val Ala Ala Ser Gly Asn Ser Gly Ala Gly Ser Ile Ser
145             150             155             160

Tyr Pro Ala Arg Tyr Ala Asn Ala Met Ala Val Gly Ala Thr Asp Gln
            165             170             175

Asn Asn Asn Arg Ala Ser Phe Ser Gln Tyr Gly Ala Gly Leu Asp Ile
            180             185             190

Val Ala Pro Gly Val Asn Val Gln Ser Thr Tyr Pro Gly Ser Thr Tyr
            195             200             205

Ala Ser Leu Asn Gly Thr Ser Met Ala Thr Pro His Val Ala Gly Ala
            210             215             220

Ala Ala Leu Val Lys Gln Lys Asn Pro Ser Trp Ser Asn Val Gln Ile
225             230             235             240

Arg Asn His Leu Lys Asn Thr Ala Thr Ser Leu Gly Ser Thr Asn Leu
            245             250             255

Tyr Gly Ser Gly Leu Val Asn Ala Glu Ala Ala Thr Arg
            260             265
```